United States Patent [19]

Hardtmann

[11] 4,015,005
[45] Mar. 29, 1977

[54] 1,2,5,6-TETRAHYDRO-4H-PYRROLO(3,2,1-ij)QUINOLIN-2-ONES

[75] Inventor: Goetz E. Hardtmann, Morristown, N.J.

[73] Assignee: Sandoz, Inc., E. Hanover, N.J.

[22] Filed: June 23, 1975

[21] Appl. No.: 589,371

Related U.S. Application Data

[63] Continuation-in-part of Ser. No. 473,778, May 28, 1974, abandoned.

[52] U.S. Cl. .......................... 424/258; 260/283 R; 260/289 R; 260/289 C
[51] Int. Cl.$^2$ ...................................... C07D 471/06
[58] Field of Search ............... 260/289 C; 424/258

[56] References Cited

UNITED STATES PATENTS 3,917,838  11/1975  Bass et al. ..................... 424/258

OTHER PUBLICATIONS

Nagarajan et al.; Tetrahedron, vol. 23, (1967) pp. 1683–1690.
Rapaport; Chem. Abst. vol. 53 (1958) 8139g.
Kato et al.; Chem. Pharm. Bull., vol. 19, pp. 832–836 (1971).

*Primary Examiner*—Donald G. Daus
*Assistant Examiner*—M. C. Vaughn
*Attorney, Agent, or Firm*—Gerald D. Sharkin; Richard E. Vila

[57] ABSTRACT

The invention discloses 1,2,5,6-tetrahydro-4H-pyrrolo-(3,2,1-ij)quinolin-2-ones having pharmacological activity in animals and useful as CNS depressant agents. The compounds may be prepared by treating a haloacetyl derivative of 1,2,3,4-tetrahydroquinoline with a Friedel-Crafts catalyst. The haloacetyl derivative of 1,2,3,4-tetrahydroquinoline may be prepared by reacting 1,2,3,4-tetrahydroquinoline with a haloacetyl halide at a mole ratio of 2:1 in the presence of an inert, organic solvent.

16 Claims, No Drawings

1,2,5,6-TETRAHYDRO-4H-PYRROLO(3,2,1-ij)QUINOLIN-2-ONES

This application is a continuation-in-part of copending application Ser. No. 473,778, filed May 28, 1974, now abandoned.

The compound 1,2,5,6-tetrahydro-4H-pyrrolo-(3,2,1-ij)quinolin-2-one, is known and has been disclosed in the literature, as found in Chem. Pharm. Bull. 19(4) 832–836 (1971), and Tetrahedron 23, 1683–1690 (1967). To my knowledge, no pharmacological activity has been heretofore associated with this compound.

The compounds which are the subject of the present invention may be represented by the following structural formula I:

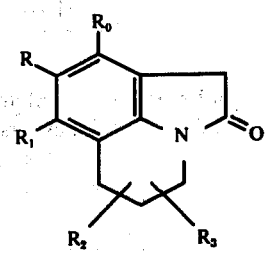

wherein
$R_2$ and $R_3$ are independently hydrogen or lower alkyl of 1 to 4 carbon atoms, and wherein
$R_0$, R and $R_1$ are independently hydrogen, halo of atomic weight of from 18 to 36, or lower alkyl of 1 to 4 carbon atoms,
with the proviso that at least one of $R_0$, R and $R_1$ is hydrogen.

As indicated above, the compound of Formula I where $R_0$, R, $R_1$, $R_2$ and $R_{23}$ are all hydrogen is known and the present invention contemplates, inter alia, the use of said compound as a CNS depressant. Novel compounds provided by the invention are those of Formula I containing at least one substituent.

The compounds of Formula I may be prepared in accordance with the following reaction scheme:

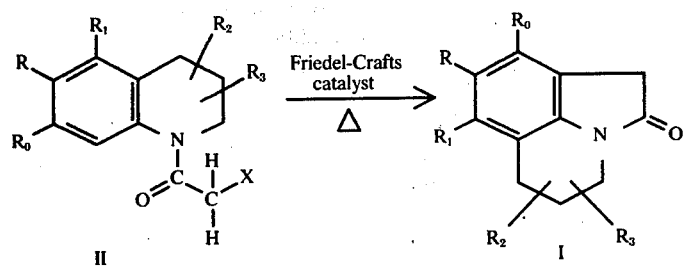

wherein $R_0$, R, $R_1$, $R_2$ and $R_3$ are as defined above and X is halogen, preferably bromine.

The compounds of formula II may be prepared by the following reaction scheme:

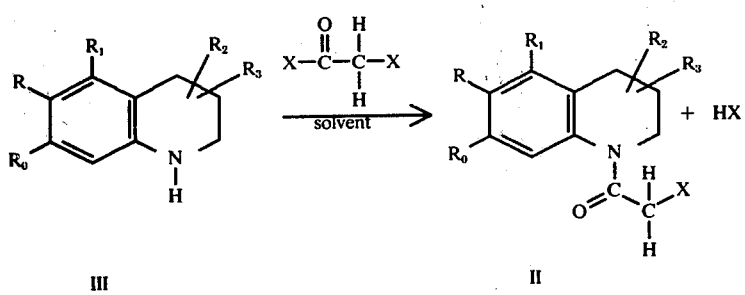

wherein $R_0$, R, $R_1$, $R_2$, $R_3$ and X are as defined above.

The preparation of compounds of formula I involves the cyclization of a haloacetyl derivative of 1,2,3,4-tetrahydroquinoline, said cyclization effected by reacting said derivative with a Friedel-Crafts catalyst at temperatures in the range of from 140° to 250° C., preferably between 180° and 210° C. Although aluminum chloride is preferred, other Friedel-Crafts catalysts, such as boron trifluoride, hydrofluoric acid and ferric chloride, may be employed. Inclusion of a solvent is optional and may be any of those typically used in Friedel-Crafts reactions, such as p-dichlorobenzene, tetrachloroethane, nitrobenzene, etc. The reaction product of formula I may be isolated from the reaction mixture by working up by conventional techniques.

The preparation of compounds of formula II involves reacting 1,2,3,4-tetrahydroquinoline with a haloacetyl halide, such as bromoacetyl bromide, by standard procedures, preferably at a mole ratio of 2:1 and generally in the presence of an inert, organic solvent which is adapted to dissolving the reactants and product compounds of formula II. Optionally, one equivalent of trialkyl amine may be added as an acid binding agent. Suitable solvents are known and available, and include by way of illustration, benzene, toluene or pyridine, a chlorinated hydrocarbon, e.g., methylene chloride, lower alkanols, e.g., ethanol and ethers, e.g., dioxane, tetrahydrofuran, etc. The reaction is preferably effected in the presence of benzene. The reaction may be carried out at temperatures in the range of from −20° to 50° C., preferably between 0° and 30° C. The resulting reaction product of formula II may be isolated from the reaction by working up by conventional techniques.

The 1,2,3,4-tetrahydroquinolines of formula III are either known or can be prepared from known materials by established procedures.

The compounds of formula I are useful because they possess pharmacological activity in animals. In particular, the compounds effect a depression of the central nervous system and are useful as minor tranquilizers as indicated by their ability to produce docility in behavior tests in mice given 10 to 200 mg./kg. i.p. of test compound according to the 30-word adjective check sheet system, basically described by S. Irwin, Gordon Research Conference, Medicinal Chemistry, 1949 and Chem. Symposium on Sedative and Hypnotic Drugs, Williams and Wilkins, 1954. For such use, the compounds may be administered orally or parenterally, preferably orally, and in admixture with conventional pharmaceutical carriers. The dosage administered may vary depending known variables such as the particular compound employed, the treatment desired and the severity of the condition being treated. In general, satisfactory results are obtained when administered at a daily dosage of from about 2 milligrams to about 150 milligrams per kilogram of animal body weight, given orally and in divided doses 2 to 4 times a day. Oral administration is preferred. For most mannals, the administration of from about 160 milligrams to about 1600 milligrams of the compound per day provides satisfactory results. For such use as tranquilizers, the compounds of Formula I are given in divided doses of from 40 to 800 milligrams, preferably 40 to 400 milligrams, 2 to 4 times a day. The compounds of Formula I are suitably administered in admixture with a solid or liquid pharmaceutically acceptable carrier or diluent.

The compounds of the Formula I are also useful as sleep-inducers as indicated by a reinduction of hexobarbital anesthesia in mice (10–200 mg./kg.) according to the method of Winter, J. Pharmacol. and Exp. Therap., 94, 7–11, 1948. The sleep-inducing effective dosage of the compounds of the Formula I will also vary depending upon known factors. However, in general, satisfactory results are obtained when the compounds are administered in a single dose at bedtime of from 2 to 150 milligrams per kilogram of body weight. For most mammals, the administration of a single dose of from 160 to 1600 milligrams provides satisfactory results and is typically administered at bedtime in admixture with a solid or liquid pharmaceutical carrier. Divided dosage forms for administration of the single dose at bedtime may be employed and contain typically 40 to 800 milligrams of the Compound I, now usually 80 to 400 milligrams.

For above uses, the compounds of structural formula I may be administered orally in such forms as tablets, dispersible powders, granules, capsules, syrups and elixirs; and parenterally as solutions, suspensions, dispersions, emulsions, and the like, e.g., a sterile injectable solution such as an aqueous suspension. These pharmaceutical preparations may contain 0.5% up to about 90% of the active ingredient in combination with the carrier or adjuvant, more usually between 10 and 60% by weight. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium phosphate, calcium sulphate dihydrate, lactose and talc, granulating and disintegrating agents, e.g., starch and alginic acid, binding agents, e.g., starch, gelatin, polyvinyl pyrrolidone and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert liquid or solid diluent, e.g., calcium carbonate, calcium phosphate, kaolin, peanut oil, sesame oil and corn oil. The preferred unit dosage forms from the standpoint of preparation and ease of administration are solid compositions, particularly hard-filled capsules and tablets. Pharmaceutical compositions in unit dosage form provided by the invention contain from 40 to 1600 milligrams of a compound I, desirably between 40 to 800 milligrams, with those containing 40 to 400 milligrams being more preferred for tranquilizer use and those containing 80 to 400 milligrams more preferred for sleep-inducer use.

Tablets and capsules containing the ingredients below may be prepared by conventional techniques and are useful in effecting tranquilization at a dose of one tablet or capsule 2 to 4 times a day.

| Ingredient | Weight (mg.) Tablet | Capsule |
|---|---|---|
| 1,2,5,6-tetrahydro-4H-pyrrolo-(3,2,1-ij)quinolin-2-one | 100 | 100 |
| tragacanth | 10 | |
| lactose | 197.5 | 250 |
| corn starch | 25 | |
| talcum | 15 | |
| magnesium stearate | 2.5 | |
| Total | 350 mg. | 350 mg. |

Representative formulations of a tablet and a capsule prepared by conventional techniques and useful in effecting sleep-induction at a dose of two tablets or capsules at bedtime are as follows:

| Ingredient | Weight Tablet | Capsule |
|---|---|---|
| 1,2,5,6-tetrahydro-4H-pyrrolo-(3,2,1-ij)quinolin-2-one | 200 | 200 |
| Tragacanth | 10 | |
| Lactose | 247.5 | 300 |
| Corn starch | 25 | |
| Talcum | 15 | |
| Magnesium stearate | 2.5 | |
| Total | 500 mg. | 500 mg. |

The following examples are merely illustrative of specific compounds of the invention and the manner in which they may be prepared.

EXAMPLE 1

1,2,5,6-Tetrahydro-4H-pyrrolo-(3,2,1-ij)quinolin-2-one

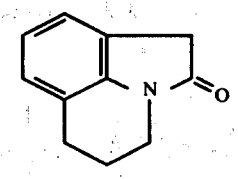

Step A: Preparation of 1-(bromoacetyl)-1,2,3,4-tetrahydroquinoline

To a stirred solution of 20.2 g. of bromoacetyl bromide in 150 ml. of benzene is added dropwise over 30 minutes, 26.6 g. of 1,2,3,4-tetrahydroquinoline dissolved in 35 ml. of benzene. The reaction mixture is then stirred at room temperature for 18 hours, after which time the precipitate is filtered off. The resultant filtrate is washed successively with 1N. HCL solution and with a saturated sodium chloride solution, dried, and the solvent removed under reduced pressure to yield 1-(bromoacetyl)-1,2,3,4-tetrahydroquinoline, b.p. 70°–80° C. (at 0.1 mm. Hg).

Step B: Preparation of 1,2,5,6-tetrahydro-4H-pyrrolo-(3,2,1-ij)quinolin-2-one

To a flask containing 30 g. of aluminum chloride is added 20.5 g. of 1-(bromoacetyl)-1,2,3,4-tetrahydroquinoline. After a vigorous initial reaction, the mixture is heated to 200° C. After 30 minutes, the reaction mixture is poured on cold water and the resulting oil is extracted with methylene chloride, dried, and the solvent removed under reduced pressure. The resultant oil is dissolved in ether, the solution cooled and the precipitate sublimed to yield 1,2,5,6-tetrahydro-4H-pyrrolo-(3,2,1-ij)quinolin-2-one, m.p. 90°–93° C.

EXAMPLE 2

Following essentially the procedure of Example 1, and using in place of 1,2,3,4-tetrahydroquinoline in Step A, an equivalent amount of
a. 6-chloro-1,2,3,4-tetrahydroquinoline,
b. 6-fluoro-1,2,3,4-tetrahydroquinoline, or
c. 6-methyl-1,2,3,4-tetrahydroquinoline,
d. 4-methyl-1,2,3,4-tetrahydroquinoline,
e. 2-methyl-1,2,3,4-tetrahydroquinoline,
there is obtained
  a. 1-(bromoacetyl)-6-chloro-1,2,3,4-tetrahydroquinoline,
  b. 1-(bromoacetyl)-6-fluoro-1,2,3,4-tetrahydroquinoline, and
  c. 1-(bromoacetyl)-6-methyl-1,2,3,4-tetrahydroquinoline,
  d. 1-bromoacetyl-4-methyl-1,2,3,4-tetrahydroquinoline,
  e. 1-bromoacetyl-2-methyl-1,2,3,4-tetrahydroquinoline, respectively.

EXAMPLE 3

Following essentially the procedure of Example 1, and using in place of 1-(bromoacetyl)-1,2,3,4tetrahydroquinoline in Step B, an equivalent amount of the respective compounds obtained in Example 2, there is obtained a. 8-chloro-1,2,5,6-tetrahydro-4H-pyrrolo-(3,2,1-ij)quinolin-2-one, m.p. 119°–20° C.
b. 8-fluoro-1,2,5,6-tetrahydro-4H-pyrrolo-(3,2,1-ij)quinolin-2-one, and
c. 8-methyl-1,2,5,6-tetrahydro-4H-pyrrolo-(3,2,1-ij)quinolin-2-one, respectively.
d. 6-methyl-1,2,5,6-tetrahydro-4H-pyrrolo-(3,2,1-ij)quinolin-2-one, m.p. 72°–75° C.
 4-methyl-1,2,5,6-tetrahydro-4H-pyrrolo-(3,2,1-ij)quinolin-2-one, m.p. 51°–54° C., respectively.

What is claimed is:

1. A pharmaceutical composition for tranquilizing or inducing sleep comprising in unit dosage form an inert pharmaceutically acceptable carrier and from 40 to 1600 milligrams of a compound of the formula:

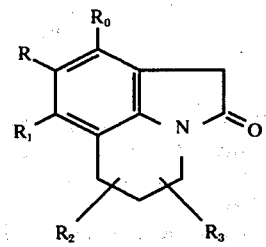

wherein
$R_0$, R and $R_1$ are independently hydrogen, fluoro, chloro or lower alkyl of 1 to 4 carbon atoms, and
$R_2$ and $R_3$ are independently hydrogen or alkyl of 1 to 4 carbon atoms,
with the proviso that at least one of $R_0$, R and $R_1$ is hydrogen.

2. A pharmaceutical composition in accordance with claim 1 in which the compound is of the formula:

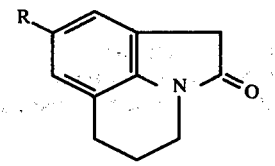

wherein R is fluoro or chloro.

3. A pharmaceutical composition in accordance with claim 1 in which the compound is of the formula:

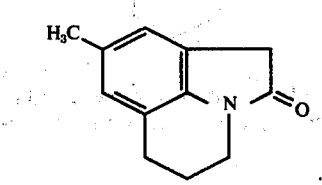

4. A pharmaceutical composition in accordance with claim 1 in which the compound is of the formula:

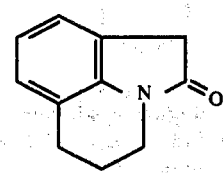

5. A pharmaceutical composition in accordance with claim 1 in solid unit dosage form and comprising from 40 to 800 milligrams of the compound.

6. The method for effecting tranquilization comprising administering to a mammal in need of such treatment a tranquilizing effective amount of a compound of the formula:

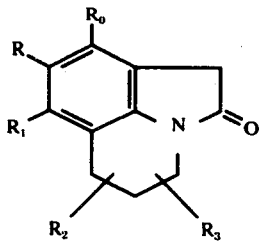

wherein
$R_0$, R and $R_1$ are independently hydrogen, fluoro, chloro or lower alkyl of 1 to 4 carbon atoms, and $R_2$ and $R_3$ are independently hydrogen or alkyl of 1 to 4 carbon atoms,
with the proviso that at least one of $R_0$, R and $R_1$ is hydrogen.

7. The method of claim 6 comprising administering a tranquilizing effective amount of a compound of the formula:

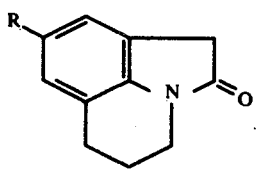

wherein R is fluoro or chloro.

8. The method of claim 6 comprising administering a tranquilizing effective amount of the compound of the formula:

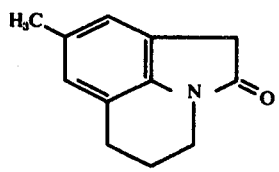

9. The method of claim 6 comprising administering a tranquilizing effective amount of the compound of the formula:

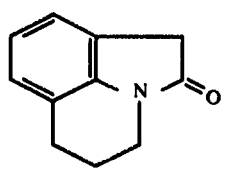

10. The method of claim 6 wherein the compound is administered at a daily dosage of from 160 to 1600 milligrams of the compound.

11. The method of claim 6 wherein the compound is administered in unit dosages from 40 to 800 milligrams of the compound.

12. The method of inducing sleep comprising administering to a mammal in need of such treatment a sleep inducing effective amount of a compound of the formula:

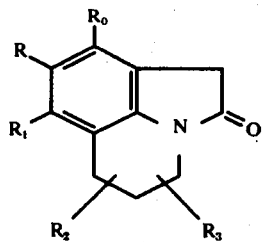

wherein
$R_0$, R and $R_1$ are independently hydrogen, fluoro, chloro, or lower alkyl of 1 to 4 carbon atoms, and $R_2$ and $R_3$ are independently hydrogen or alkyl of 1 to 4 carbon atoms,
with the proviso that at least one of $R_0$, R and $R_1$ is hydrogen.

13. The method of claim 12 comprising administering a sleep-inducing effective amount of a compound of the formula:

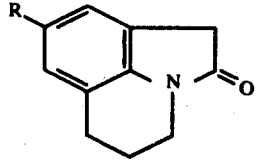

wherein R is fluoro or chloro.

14. The method of claim 12 comprising administering a sleep-inducing effective amount of the compound of the formula:

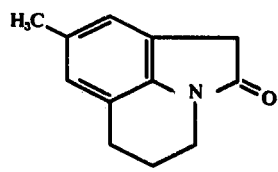

15. The method of claim 12 comprising administering a sleep-inducing effective amount of the compound of the formula:

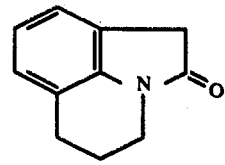

16. The method of claim 12 wherein the compound is administered in an amount of from 160 to 1600 milligrams at bedtime.

* * * * *